United States Patent
Bell et al.

(10) Patent No.: US 8,308,725 B2
(45) Date of Patent: Nov. 13, 2012

(54) REVERSE SEALING AND DISSECTION INSTRUMENT

(75) Inventors: Stephen G. Bell, Rome (IT); Wayne A. Noda, Mission Viejo, CA (US)

(73) Assignee: Minos Medical, Irvine, CA (US)

( * ) Notice: Subject to any disclaimer, the term of this patent is extended or adjusted under 35 U.S.C. 154(b) by 960 days.

(21) Appl. No.: 12/050,280

(22) Filed: Mar. 18, 2008

(65) Prior Publication Data

US 2008/0312652 A1  Dec. 18, 2008

Related U.S. Application Data

(60) Provisional application No. 60/895,907, filed on Mar. 20, 2007.

(51) Int. Cl.
*A61B 18/18* (2006.01)

(52) U.S. Cl. ............... 606/52; 606/49; 606/50; 606/51; 606/205

(58) Field of Classification Search ............ 606/40–42, 606/45, 49–50, 51–52, 144, 147, 169, 205–208; 433/4, 158, 159; 294/104, 106; 81/92, 97, 81/99, 111, 304, 306, 309, 314–325, 341–345, 81/354
See application file for complete search history.

(56) References Cited

U.S. PATENT DOCUMENTS

| | | | |
|---|---|---|---|
| 2,541,246 A * | 2/1951 | Held .......................... 606/205 |
| 2,738,790 A | 3/1956 | Todt, Sr. et al. |
| 5,112,346 A | 5/1992 | Hiltebrandt et al. |
| 5,195,505 A | 3/1993 | Josefsen |
| 5,217,460 A * | 6/1993 | Knoepfler .................... 606/52 |
| 5,219,358 A | 6/1993 | Bendel et al. |
| 5,431,323 A | 7/1995 | Smith et al. |
| 5,443,475 A * | 8/1995 | Auerbach et al. ........... 606/170 |
| 5,458,609 A | 10/1995 | Gordon et al. |
| 5,620,459 A * | 4/1997 | Lichtman ................... 606/205 |
| 5,649,947 A * | 7/1997 | Auerbach et al. ........... 606/170 |
| 5,718,703 A * | 2/1998 | Chin ............................ 606/49 |
| 5,785,707 A | 7/1998 | Boyd et al. |
| 5,899,909 A | 5/1999 | Claren et al. |
| 6,332,888 B1 | 12/2001 | Levy et al. |
| 6,382,214 B1 | 5/2002 | Raz et al. |
| 6,443,970 B1 * | 9/2002 | Schulze et al. .............. 606/171 |
| 6,475,135 B1 | 11/2002 | Levy |
| 6,623,482 B2 | 9/2003 | Pendekanti et al. |

(Continued)

FOREIGN PATENT DOCUMENTS

WO    9800069    1/1998

(Continued)

*Primary Examiner* — Michael Peffley
*Assistant Examiner* — Khadijeh Vahdat
(74) *Attorney, Agent, or Firm* — John L. Rogitz (57) ABSTRACT

The invention relates to a device and related method for sealing and/or dissecting body tissue using a reverse action instrument. The devices and methods described permit laparoscopic or natural body orifice access to an anatomical space and facilitate sealing portions of tissue together, dissecting tissue or combinations thereof. A surgical instrument for sealing and dissecting body tissue is described having distal and proximal ends with an elongated body. The body includes a jaw member positioned at the distal end that is defined by a stationary arm and a pivotable arm. A moveable closure sleeve is disposed at least partially about the body and the closure sleeve is configured such that coaxial movement of the sleeve along the longitudinal axis of the body causes the jaw member to open or close.

29 Claims, 5 Drawing Sheets

U.S. PATENT DOCUMENTS

| | | | |
|---|---|---|---|
| 6,652,521 B2 * | 11/2003 | Schulze | 606/45 |
| 6,699,243 B2 | 3/2004 | West et al. | |
| 6,709,386 B2 | 3/2004 | Smid et al. | |
| 6,802,840 B2 | 10/2004 | Chin et al. | |
| 6,858,028 B2 | 2/2005 | Mulier et al. | |
| 6,911,003 B2 | 6/2005 | Anderson et al. | |
| 6,936,054 B2 | 8/2005 | Chu | |
| 6,984,237 B2 | 1/2006 | Hatch et al. | |
| 7,063,699 B2 * | 6/2006 | Hess et al. | 606/51 |
| 7,131,943 B2 | 11/2006 | Kammerer | |
| 7,229,453 B2 | 6/2007 | Anderson et al. | |
| 7,278,992 B2 | 10/2007 | Cropper et al. | |
| 7,303,560 B2 | 12/2007 | Chin et al. | |
| 7,338,502 B2 | 3/2008 | Rosenblatt | |
| 7,445,621 B2 * | 11/2008 | Dumbauld et al. | 606/51 |
| 2002/0026127 A1 * | 2/2002 | Balbierz et al. | 600/567 |
| 2002/0099375 A1 * | 7/2002 | Hess et al. | 606/51 |
| 2003/0018331 A1 * | 1/2003 | Dycus et al. | 606/48 |
| 2003/0195498 A1 | 10/2003 | Treat et al. | |
| 2004/0015155 A1 | 1/2004 | Whalen et al. | |
| 2004/0054353 A1 | 3/2004 | Taylor | |
| 2004/0144395 A1 | 7/2004 | Evans et al. | |
| 2004/0204718 A1 * | 10/2004 | Hoffman | 606/108 |
| 2005/0215996 A1 | 9/2005 | Ouchi | |
| 2005/0250977 A1 | 11/2005 | Montpetit et al. | |
| 2006/0030848 A1 * | 2/2006 | Craig et al. | 606/49 |
| 2006/0058575 A1 | 3/2006 | Zaddem et al. | |
| 2006/0083767 A1 | 4/2006 | Deusch et al. | |
| 2006/0200175 A1 * | 9/2006 | Griffiths | 606/139 |
| 2006/0258898 A1 | 11/2006 | Montpetit et al. | |
| 2006/0282105 A1 | 12/2006 | Ford et al. | |
| 2007/0239208 A1 | 10/2007 | Crawford | |
| 2007/0255268 A1 | 11/2007 | Nobis et al. | |
| 2007/0255277 A1 | 11/2007 | Nobis et al. | |
| 2007/0255278 A1 | 11/2007 | Nobis et al. | |
| 2007/0260179 A1 | 11/2007 | Sholev et al. | |
| 2007/0270797 A1 | 11/2007 | Lu et al. | |
| 2007/0270890 A1 | 11/2007 | Miller | |
| 2008/0109015 A1 | 5/2008 | Chu et al. | |

FOREIGN PATENT DOCUMENTS

| | | |
|---|---|---|
| WO | 03096929 | 11/2003 |
| WO | 2004012579 | 2/2004 |
| WO | 2006108145 | 10/2006 |
| WO | 2007109508 | 9/2007 |
| WO | 2007149348 | 12/2007 |

* cited by examiner

REVERSE SEALING AND DISSECTION INSTRUMENT

CLAIM OF PRIORITY

This application claims priority under 35 U.S.C. §119(e) to U.S. Provisional Application No. 60/895,907, filed Mar. 20, 2007, the entire contents of which are hereby expressly incorporated by reference.

FIELD OF THE INVENTION

The invention relates to a device and related method for sealing and/or dissecting body tissue using a reverse action instrument. The devices and methods described permit laparoscopic or natural body orifice access to an anatomical space and facilitate sealing portions of tissue together, dissecting tissue or combinations thereof.

BACKGROUND OF THE INVENTION

Laparoscopic and endoscopic surgical procedures are minimally invasive procedures in which operations are carried out within the body by means of elongated instruments inserted through small entrance openings in the body. These procedures are less invasive leading to reduced surgical trauma, lower costs and quicker recovery times than conventional surgery. However this requires that the surgeon operate in narrow spaces with small areas for maneuvering and with limited visibility using endoscopes.

In these procedures often portions of tissue must be sealed, dissected or sealed and dissected as part of the procedure. When this is performed inside body cavities having narrow operating areas this tissue manipulation can be difficult. Conventional sealing and dissecting instruments utilized in most of these procedures are forward facing cutting instruments such as scissors, blades or bipolar or single polar electrodes. These types of cutters are best utilized with an off axis endoscope so that the cutting head of the instrument is visible throughout the procedure. However if the cutting instrument is placed through the working channel of the endoscope or alongside the endoscope, the actions of a forward facing cutter are not always visible. The lack of visibility can result in less precise tissue dissection and the added risk of tissue dissection that is undesired. Additionally some areas of tissue removal cannot be approached with a forward cutting device. The surgeon must either work awkwardly with a forward cutting instrument or create an instrument portal close to the viewing portal which can make triangulation of the work awkward and difficult.

Therefore a reverse acting sealing and cutting device would be advantageous that will operate in a manner such that the surgeon can easily visualize the operational area without the cutting head obstructing the endoscopic view. This type of cutter should have a simple sealing and cutting mechanism and should be easily activated by the surgeon from outside the patient. Other reverse acting cutters have been previously described such as that described by Auerbach (U.S. Pat. No. 5,649,947) and others but these are primarily cutters and graspers only. These do not describe the need to seal tissue before cutting so that body channels are sealed off and body fluids such as blood vessels contained. Furthermore these described cutters utilize cams and long cable and rod actuators that are cumbersome, bulky and mechanically complex to operate and manufacture. A need exists therefore for improved instruments for sealing and dissecting tissue inside the body that utilize a reverse acting activation head. Additionally a need exists for an improved device for sealing tissue before cutting the tissue. Finally there exists a need for a simple to operate reverse acting cutter that utilizes a simple mechanical mechanism for effectively removing body tissue.

SUMMARY OF THE INVENTION

The present invention may solve the needs in the art stated above and may provide certain advantages over the prior art. The present invention may improve upon other available endoscopic cutting instruments and facilitate tissue removal from the body by incorporating tissue sealing and dissection in a single instrument. Furthermore the instrument may accomplish this with a simple to use backward facing activation system that permits finite control combined with superior dissection capabilities.

An object of the present invention is to provide a surgical instrument for sealing and dissecting body tissue having distal and proximal end portions including an elongated body having a longitudinal axis and an outside diameter, a jaw member positioned at the distal end portion with the jaw member having a stationary arm formed in the body and a pivotable arm coupled to the distal end portion of the body. The instrument may further have a moveable closure sleeve that is disposed at least partially about the body of the instrument with the closure sleeve configured such that coaxial movement of the sleeve along the longitudinal axis causes the jaw member to open or close. The jaw member described may be configured such that the jaw opening generally opens toward the proximal end portion of the elongated body.

In another embodiment of the invention the jaw member is adapted so that movement of the closure sleeve causes the pivotable member to open or close and the jaw member may be further configured with a spring that may bias the pivotable member into an open configuration. Additionally the jaw member described may be configured to articulate and rotate about a longitudinal axis of the elongate body to facilitate capturing body tissue in the jaw member.

In another embodiment of the present invention the closure sleeve may further comprise a closure ring that defines a distal edge of a treatment window. This window may be positioned at the distal end portion of the sleeve and the closure ring may be adapted to contact the pivotable member and cause the member to pivot closed when the ring is moved toward the proximal end portion.

In an additional aspect of the present invention the jaw member further comprise at least one tissue modification member on the stationary arm, the pivotable arm, the elongate body or a combination thereof. The modification member may be capable of sealing, dissecting or a combination of sealing and dissecting body tissue positioned between the stationary arm and the pivotable arm.

In another embodiment of the present invention the tissue modification member may be a dissecting blade attached to the pivotable arm with the blade configured to dissect tissue positioned between the pivotable arm and the stationary arm.

In another embodiment of the present invention the tissue modification member may be a moveable dissecting blade positioned inside the distal end portion of the elongate body with the blade adapted to slide along the longitudinally axis of the elongate body to dissect body tissue confined between the arms of the jaw member.

In another embodiment of the present invention the tissue modification member has at least one energy director which is configured so that when energy from an energy source is passed through the energy director, body tissue confined between the two arms is sealed, dissected, or a combination of sealed and dissected.

In one embodiment of the present invention the energy source is an ultrasonic source or a monopolar, bipolar or tripolar source or a dc current source.

In another aspect of the invention the tissue modification member may include a controller such that the order of sealing and dissecting can be controlled by an operator from outside the body. In another embodiment of the present invention the tissue modification member may comprise at least a first and a second energy director that is attached to each of the pivotable arm and the stationary arm. The energy directors may be aligned so that when the jaw member closes the first energy directors form an opposing pair and the at least second energy directors form an opposing pair. These pairs of opposing conductors may seal, dissect or perform a combination of sealing and dissecting on tissue located in between the two arms when energy from an energy source is passed between the opposing pairs of energy directors.

In another embodiment of the present invention these pairs of opposing conductors may seal, dissect or perform a combination of sealing and dissecting on tissue located in between the two arms when energy from an energy source is passed between the first energy director attached to the pivotable arm and the second energy director attached to a stationary arm.

Another object of the present invention is to provide a surgical instrument for sealing and dissecting body tissue that has distal and proximal end portions including an elongate body with a reverse acting jaw member coupled at the distal end portion with the jaw member biased in an open position. The jaw member may be formed by one stationary arm which is a part of the elongate body and a second arm that is pivotably connected at the distal end portion and generally oriented toward the proximal end portion. The jaw member may be configured to be activated by a closure sleeve coaxially disposed about the elongated body such that the jaw may be opened and closed by movement of the sleeve along a longitudinal axis of the elongated body. In another embodiment, the above described closure sleeve is a tube that surrounds the elongate body and the sleeve may have an activation portion that is defined by an opening in the sleeve. The opening may be sized and adapted so that when the activation portion is aligned with the jaw member, the jaw member is in an open configuration and when the sleeve is moved toward the proximal end portion, the jaw member is moved toward a closed configuration. The elongated body may also have a tunneling tip positioned at the distal end portion and adapted to facilitate placement of the instrument through body tissue.

A further object of the present invention is a method for sealing or dissecting body tissue with a surgical instrument having proximal and distal ends including the steps of inserting the instrument having an elongated body with a hinged jaw member coupled to the distal end into an internal body space. The hinged jaw of the instrument has a stationary arm and a pivotable arm with the jaw opening generally oriented toward the proximal end of the instrument. The method further includes sliding a closure sleeve that is partially disposed around the elongated body and the closed hinged jaw toward the distal end to release the pivotable arm of the hinged jaw member into an open configuration, positioning body tissue in the jaw member and sliding the closure sleeve toward the proximal end to move the pivotable arm of the hinged jaw member into a generally closed configuration about the body tissue. The method further includes activating a tissue modification member to seal tissue together or dissect tissue or a combination of sealing and dissecting tissue.

A further object of the invention is a method utilizing at least a first and a second energy director attached to each of the pivotable arm and the stationary arm with the energy directors aligned so that when the jaw member closes the first energy directors form an opposing pair and the second energy directors form an opposing pair.

Another aspect of the invention is a method for use in sealing or dissecting body tissue in abdominal surgery with a surgical instrument having proximal and distal ends including the steps of inserting the instrument through a natural body opening and through an internal body wall and into an abdominal cavity, opening a jaw member coupled to the distal end the instrument by distally advancing a closure sleeve that is coaxially disposed about the instrument and the jaw member. The method further includes positioning the jaw member so that tissue is positioned in the jaw member, closing the jaw member on the tissue by proximally retracting the closure sleeve, activating a tissue modification member on the jaw member or the elongate body and releasing the jaw member.

It is understood that both the foregoing general description and the following detailed description are exemplary and explanatory only and are not restrictive of the invention as claimed. The accompanying drawings illustrating an embodiment of the invention and together with the description serve to explain the principles of the invention.

DETAILED DESCRIPTION OF THE PREFERRED EMBODIMENTS

Figure 1A:
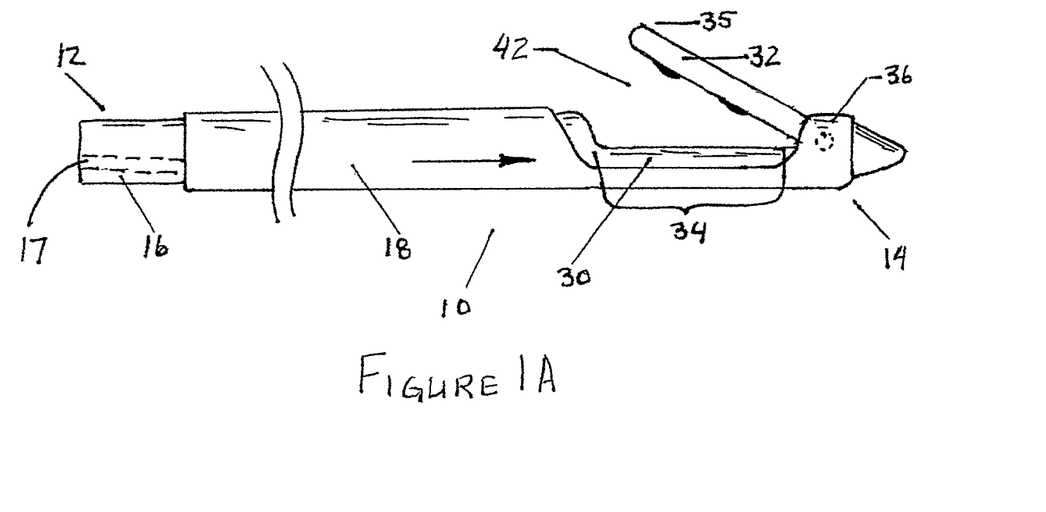
FIG. 1A is a perspective view of the instrument of the present invention in the open configuration.

Although several different methods of sealing and cutting body tissue are known in the art, accessing certain anatomical cavities in the body that may have limited accessibility and visibility and then sealing and/or cutting through tissue is difficult. Therefore an improved tissue sealer and cutting instrument is described that facilitates tissue removal inside small areas of the body by employing a reverse cutter. This cutter may facilitate tissue removal by improving visualization of the cutting procedure. When the cutter is reverse directed, that is to say that the jaws of the cutter open toward the proximal end of the instrument rather than away from the proximal end of the instrument the operator may more easily visualize the cutting process especially if the endoscope is inserted along the longitudinal axis of the instrument. This and other advantages of this type of cutter will be appreciated as shown in the drawings. Referring to the FIGS. 1-10, an instrument 10 is shown having a proximal end portion 12 and a distal end portion 14. The instrument is comprised of an elongated tube 16 that traverses from the proximal end portion 12 which resides outside the patient's body to the distal end portion 14 which is inserted into the patient. The elongated tube has a longitudinal axis and an outside diameter sized for introduction into various cavities and spaces in the body. The elongated body 16 may be a solid shaft, a flexible shaft and may incorporate other lumens 17 as shown in FIG. 1A. The instrument may also be sized so that it may be introduced into the body through the working lumen of an endoscope. The shaft may be torqueable, that is it may be capable of transmitting a torque applied at the proximal end portion and transmitting that applied torque to the distal end portion 14 so that the distal end portion 14 rotates in response to the applied torque. Likewise the body may have one or more articulated segments that can be moved by the operator so that the orientation and the direction of the elongated body can be steered by the operator to a particular site of interest in the body. These articulation joints and mechanisms are not shown but are well known by those skilled in the art.

The elongated body 16 is fitted inside a moveable closure sheath 18 that is coaxial with the elongated body 16 and extends from the proximal end portion 12 to the distal end portion 14. The moveable closure sheath 18 is made from a thin walled material that is configured to fit closely over the elongated body while keeping the outside diameter of the sheath as small as possible. This may be important so that the overall diameter of the instrument is minimized so that the instrument is maneuverable for insertion into the body and subsequent placement at the targeted interventional site. The instrument may be particularly designed for use with natural orifice transluminal endoscopic surgery (NOTES). In these procedures, small instrument are delivered to various cavities or spaces in the body but particularly into the abdominal cavity through natural orifices of the body. These natural orifices are generally considered to be the esophagus, colon, and bladder and may include transvaginal approaches as well.

The proximal end of the body 16 and closure sheath 18 are connected to a handle (not shown) at their proximal ends. The handle has an actuator that can be activated to move the sheath 18 relative to the body 16 by the operator. A jaw member 20 is located at the distal end portion of the body 18. The jaw member 20 is comprised of two arms, a stationary arm 30 and a pivotable arm 32. The stationary arm 30 is preferably formed as part of the body 16. At the distal end portion 14 of the body a cavity 34 may be formed and the stationary arm 30 may be formed in this cavity 34 and may be essentially integral to the body itself. The stationary arm 30 may also be a separate structure that is positioned inside the cavity 34. The stationary arm 30 does not move inside the cavity and its position may remain relatively fixed. The stationary arm 30 may include other devices or apparatus as part of its function.

The pivotable arm 32 has a proximal end 35 and a distal end 36. This arm 32 is coupled to the distal end portion of the body 16 by a pivot point 38 located at the distal end 36 of the pivotable arm 30. This pivot point 38 permits the movement of the pivotable arm about this point so that the pivotable arm 32 may act as a jaw in conjunction with the stationary arm 30. The proximal end 35 of the pivotable arm 32 is unattached and is free to rotate about pivot point 38. The pivotable arm 32 is attached at pivot point 38 by a hinge pin 40. The jaw member 20 is designed so that it is a reverse acting jaw with the opening of the jaw 42 formed by the proximal end 35 of the pivotable arm 32 and stationary arm 30 generally directed towards the proximal end portion 12 of the instrument 10. As will be shown the pivotable arm 32 is prevented from opening in a different direction or from excessive pivoting about pivot point 38.

This particular embodiment may be an important feature of the invention because the direction of the manipulation of tissue for reverse acting instruments is generally toward the instrument body and not away from the instrument body. As the reverse acting jaw engages, captures and manipulates tissue the forces of such manipulation are toward the instrument. This ability to "hook" the tissue places the tissue in constant tension which aids in dissection. These forces also tend to confine tissue and pull it towards the interventional instrument. This means that the operator does not need to chase down tissue that needs to be manipulated or is not continually cutting away from the instrument. This may be particularly important with NOTES procedures because often the endoscope is inserted along the same axis as the instrument itself. Therefore with conventional forward acting cutters it is difficult to visualize the sealing or cutting of tissue that is at the end of the instrument. Reverse acting cutters however direct the action of the manipulation of tissue toward the endoscope and the operator's field of view. This may facilitate more accurate and timely removal of tissue or the performance of other interventional procedures.

Additionally by having a reverse cutter, dissection can begin at the deep boundary of the structures and then proceed in a downward direction. This type of surgical approach is often performed with less invasive vaginal hysterectomy (LAVH) procedures. In this approach, tissue and organ structures can be dissected in a more anatomically advantageous way. For example with this dissection technique, as the cutter dissects away tissue, a wider V is created as the dissection proceeds thus allowing improved access with each subsequent dissection. A convention forward facing cutter dissects from the opposite direction which requires working in a smaller space first. This may makes surgery more difficult, time consuming and less safe.

The pivotable arm 32 may have a spring 50 positioned against the arm 32 and the stationary arm 30. This spring 50 may be a coil spring or a leaf spring or may be formed integrally with the pivotable arm 32 such as a "living hinge". This spring 50 biases the jaw member 20 and in particular the pivotable arm 32 in an open configuration so that the pivotable arm will open up in a direction "P" as shown in FIG. 1C unless restrained. This insures that the jaw member will open up if a restraining force is removed from the jaw member 20.

The distal end of the moveable closure sleeve 18 has a treatment window 54 that generally overlays the cavity 34 of the elongated body. The treatment window 54 is an opening in the sleeve 18. This window 54 is sized so that when the window is positioned so that it overlays the pivotable arm 32, the restraining force on the pivotable arm caused by the closure sleeve 18 is removed and the pivotable arm 32 opens in response to the spring bias. As can be understood, as the closure sleeve 18 is moved in a distal direction along the longitudinal axis of the body 16 as shown by the distal facing arrow in FIG. 1A and the treatment window aligns with pivotable arm 32, the arm 32 opens. As the as the closure sleeve 18 is moved in a proximal direction along the longitudinal axis of the body 16 as shown by the proximal facing arrow in FIG. 1B and the alignment of the treatment window 54 with the pivotable arm 32 is removed, the arm 32 gradually closes until it assumes a closed configuration.

A specialized tunneling tip 55 is attached to the elongated body or may be integrally formed with the body at the distal end portion of the body. This tunneling tip defines a generally pointed tip that is adapted to tunnel through tissue so that the elongated body 16 may be placed into the abdominal cavity or other cavity in the body. The tip is suited for transversing tissue planes so that the instrument 10 may be directly placed into the body through tissue walls without the need for a separate introducer. In a preferred embodiment, the tunneling 55 tip has a generally blunt tip that enables blunt dissection to advance the instrument through tissue, adhesions, fat, etc. This may minimize accidental dissection of vessels, nerves and other structures when inserting the instrument.

The distal end portion of the treatment window 54 defines a closure ring 56 which is an annular portion of the closure sleeve 18 at the distal end of the treatment window. This ring 56 engages the pivotable arm 32 and forces the arm 32 closed when the sleeve is moved proximally and gradually allows the arm 32 to open as the sleeve is moved distally. The ring 56 may be reinforced with a metallic or polymeric insert.

The degree of movement permitted for the pivotable arm 32 is controlled by the amount of distal movement of the closure ring 56. The instrument 10 may have limit stops that regulate the length of travel of the closure sleeve so that the angle of the jaw member opening is restricted. This movement may be controlled by the handle and the amount of movement of the sleeve 18 may be calibrated so that the angle of the jaw member opening can be precisely known by the displacement of the sleeve 18 relative to the body 16.

Figure 1B:
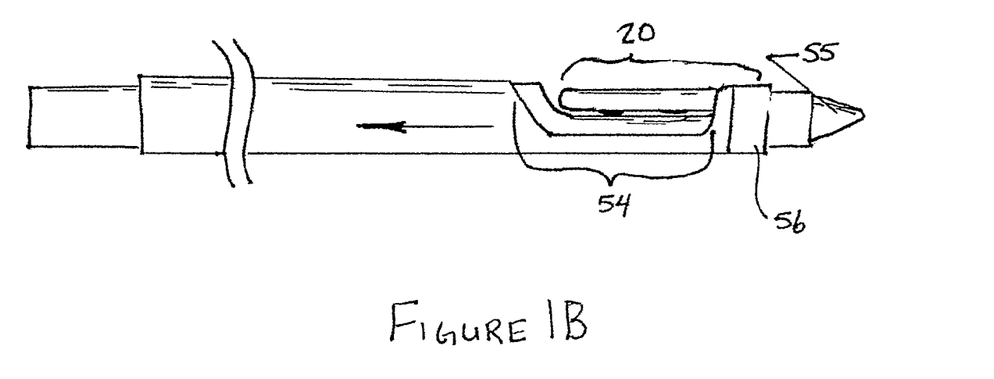
FIG. 1B is a perspective view of the instrument of the present invention in the closed configuration.
Figure 1C:
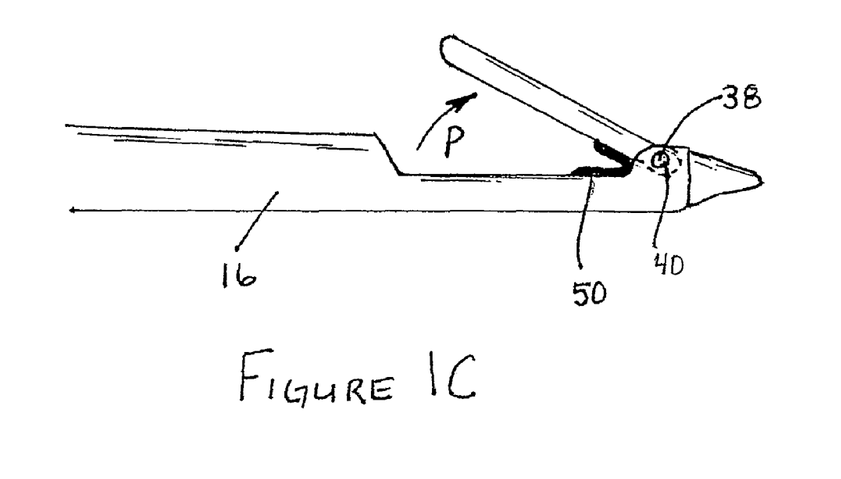
FIG. 1C is a perspective view of the instrument showing the biasing spring.

As shown in FIG. 1B, the jaw member 20 or in particular the pivotable arm 32 is sized in conjunction with the cavity 34 so that when the arm 32 is in the closed configuration, the outside diameter of the jaw member is the same as or smaller than the outside diameter of the elongated body 16. This insures that when the closure sleeve 18 is completely retracted in the proximal direction, the jaw member 20 is contained within the inside diameter of the body 16.

Figure 2:
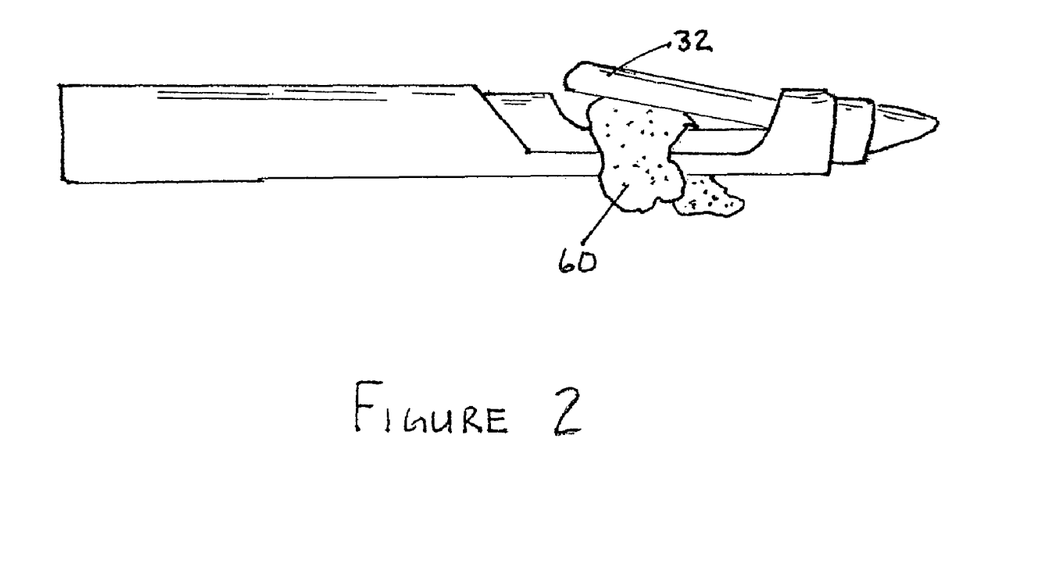
FIG. 2 is a detail drawing of an access device of FIG. 1 with tissue confined between two jaw members.

The closure sleeve 16 and the closure ring 56 can be used to apply considerable clamping force to tissue captured in the jaw member 20. When tissue is positioned in the open jaw member 20 between the stationary arm 30 and the pivotable arm 32, as the closure ring is moved proximally a greater restraining force is applied to the pivotable arm 32. This increasing restraining force closes the jaw member and captures tissue 60 between arms 30 and 32. This is shown in FIG. 2. The arm 32 is shown partially closed because the bulk of the tissue 60 may prevent complete closure. However in this configuration the closure ring can still apply a restraining force (i.e. a clamping force) to the pivotable arm 32. This may be important for effective tissue manipulation. As the tissue is manipulated or more preferably as energy is applied to the tissue the tissue often shrinks in size. This may be a result of the vaporization of the water in the tissue or migration of the water into other areas of the tissue. As the tissue shrinks, increasing amounts of clamping force may be required to capture the tissue in the jaw members. The closure sleeve 18 can continually moved in a proximal direction to apply a continually increasing clamping force as required. When the tissue manipulation results in dissection of the tissue, the arm 32 completely contacts the stationary arm 30 and is in the closed configuration, the closure sleeve 18 may completely slide over the pivoting arm 32 and the instrument can be withdrawn or repositioned for additional intervention.

Figure 8:
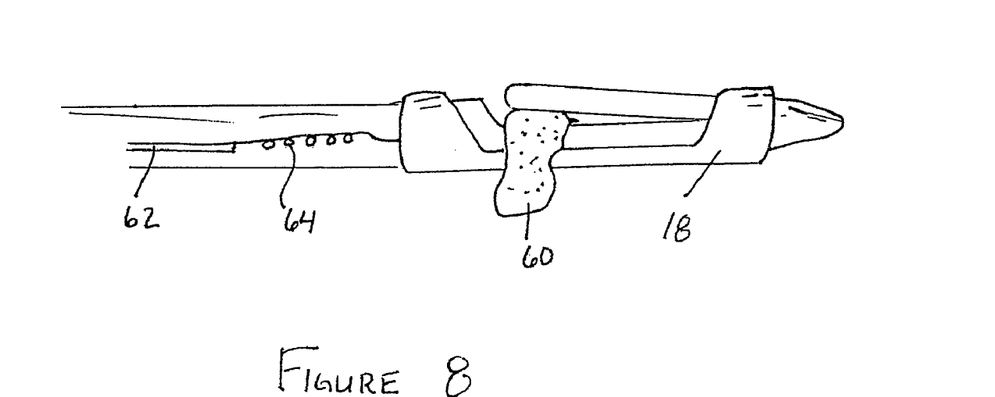
FIG. 8 is a side section view of the instrument showing one embodiment of an actuator with an attached spring.

In one embodiment of the invention shown in FIG. 8, the closure sleeve 18 may be manipulated by an actuator 62 that is linked between the closure sleeve and the proximal handle. This actuator 62 may have a tension spring 64 positioned between the actuator 62 and the closure sleeve 18. The actuator may be used to retract the closure sleeve and the spring may be used to apply a constant closure or clamping force to the pivotable arm 32. This may be important so that a constant clamping force is applied as tissue 60 shrinks due to tissue manipulation. In this embodiment the instrument 10 would self adjust so that a constant and uniform clamping force is applied on the arm 32 and the tissue 60. In this case the operator would not need to constantly increase the force as the tissue shrinks but could rely on the spring 64 to apply this adjusting force.

The instrument described 10 may be used to manipulate tissue using the jaw member 20. In this embodiment of the invention, manipulations of tissue may be used to seal, coagulate or dissect tissue or any combination of sealing, coagulating or dissecting. In one embodiment of the invention the instrument can be used to seal tissue. In another embodiment the instrument may be used to seal and then dissect tissue and in other embodiments the instrument may be a dissection instrument only. Preferably the instrument is used to seal tissue first before dissecting the tissue. When the tissue is sealed, the blood vessels, ducts and channels can be sealed thus avoiding any loss of blood or body fluids from a subsequent dissection of the tissue. Additionally, when tissue is sealed by applying energy, the tissue shrinks in size and the dissection may be more effective. For example, if a blood vessel is to be dissected, sealing the dissection zone first permits the blood vessel to be dissected without subsequent loss of blood from the vessel because the vessel ends are sealed shut. In the case of a volume reduction of a partially diseased organ, first sealing around the intended dissection area of an organ, permits the subsequent dissection of a diseased portion of the organ while keeping the remainder of the organ viable.

Figure 3:
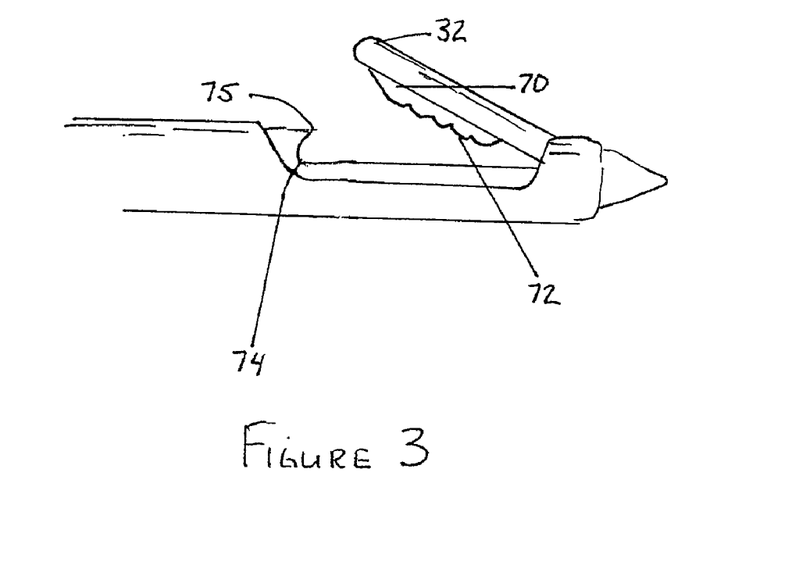
FIG. 3 is a perspective view of the instrument showing the dissecting blade.

As shown in FIG. 3, the jaw member 20 may have a tissue manipulation member 70 positioned on the stationary arm 30, on the pivotable arm 32 or a combination of these arms. The arms 30 and 32 may have more than one tissue modification member positioned on each arm with potentially different types or methods of tissue modifications possible. This tissue modification member is adapted to modify the characteristics of the tissue 60 that comes in contact with this member 70. The tissue modifications may include heating, mechanical, chemical or radiation ablation, tearing, dissecting, staining, sealing, marking with an isotope or freezing. Other tissue modifications that are typically performed in endoscopic procedures other than those described are also anticipated.

As shown in FIG. 3, the tissue modification member may be a dissecting blade 72 that is attached to the pivotable arm 32. The dissecting blade 72 in this embodiment has a sharpened edge that may be used to dissect tissue as the blade is closed around the tissue 60. As can be appreciated, as the blade is moved from an open configuration to a closed configuration, the blade 72 impinges on the tissue positioned in the open jaw member 20 and slices the tissue into two sections. A grasper 74 may be formed into the proximal edge of the treatment window and may be constructed so that it has an overhanging lip 75. This lip may be useful to retain the tissue in the treatment window. As tissue is dissected, the tissue may have a tendency to move in the direction of cutting and the lip and the grasper may help retain the tissue by preventing the tissue from sliding out of the proximal edge of the treatment window. Similarly, the proximal edge may also have a roughened, serrated edge or may have other mechanical features that grip the tissue and help prevent slippage out of the treatment window as well.

Figure 4A:
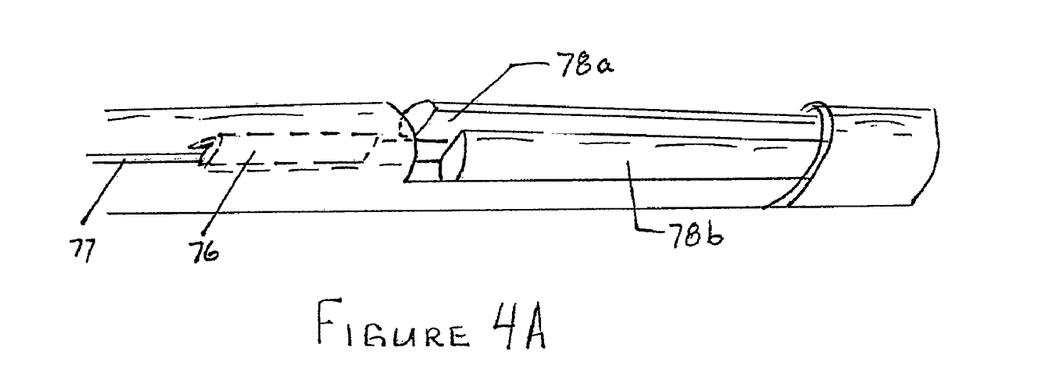
FIG. 4A is a perspective view of the instrument showing the moveable dissecting blade in the retracted position.
Figure 4B:
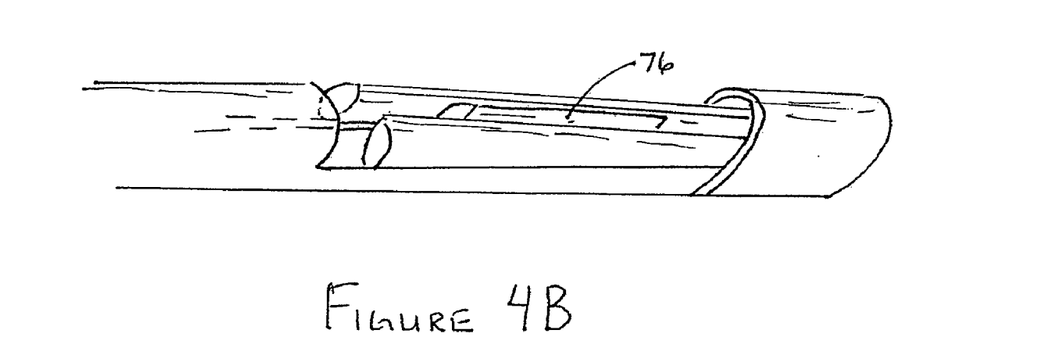
FIG. 4B is a perspective view of the instrument showing the moveable dissecting blade in the extended position.
Figure 5:
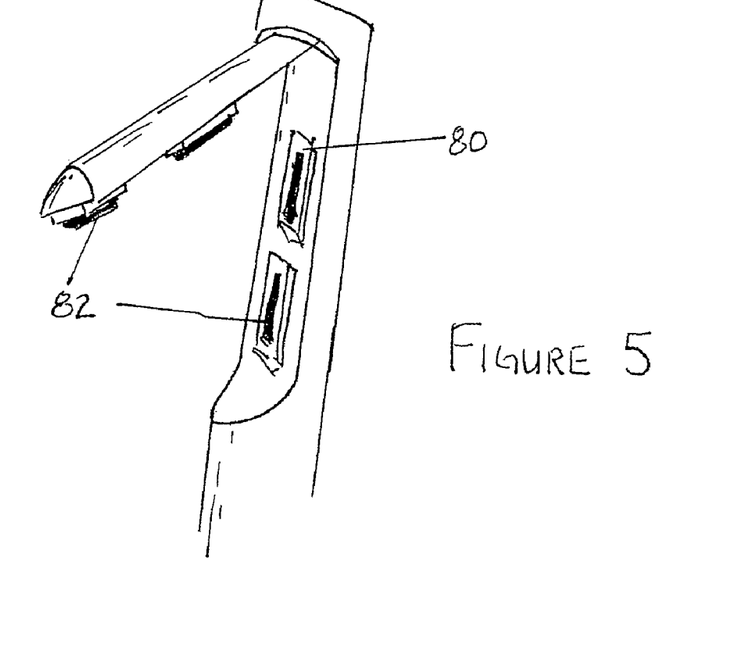
FIG. 5 is perspective view of the jaw member showing the tissue modification member and energy director.

Another embodiment of the tissue modification member 70 is shown in FIG. 4A. In this embodiment the tissue modification member 70 is a sliding dissection blade 76 attached to actuating element 77 that extends from the dissecting blade 76 at one end to the proximal end portion 12 of the elongated body at the other end. The proximal end of this actuating element 77 may be attached to a handle (not shown) so that the displacement of the actuating element 77 can be controlled by the operator. The dissection blade 76 in this embodiment can be moved independently of the jaw member 20 by moving the actuating element. As shown in FIG. 4B, the pivotable arm may be divided into two halves 78a and 78b so that the blade 76 can slide between the two arm halves to dissect tissue that is captured by the jaw member 20. Alternatively the bottom surface of the pivotable arm 32 and the corresponding portion of the stationary arm 30 may have a groove or a relief adapted to accommodate the sliding dissecting blade. This groove may be preferentially located in the pivotable arm 32, the stationary arm 30 or in both arms. This groove may also be used to provide a track or guide along with dimensional clearance so that the blade may pass through tissue confined by the jaw member 20. Referring to FIGS. 5 and 6, there is shown another embodiment of the invention where at least one tissue modification member 80 is positioned on the pivotable arm 32, the stationary arm 30 or both arms. The tissue modification member 80 in this embodiment has at least one energy director 82 coupled to the tissue modification member. This energy director may be adapted to channel or direct energy applied to it into the tissue positioned between the jaw member 20. The energy director may consist of a single solitary director 82 or multiple energy directors that may be positioned along either or both of the arms 30 and 32. The energy directors may be randomly positioned on the arms. The energy directors may be arranged in couplets so that a director 82 attached to one arm may have a corresponding mating director located on the other arm. These couplets may be directly opposed from each other when both arms are in the closed configuration. These couplets may also be slightly offset from each other when both arms are in the closed configuration. This offset may be several tenths of a millimeter up to several millimeters. Alternatively, on the same arm, some of the energy directors may be couplets as described previously with opposing corresponding directors on the opposing arm and others may be single energy directors that have a preset offset from other energy directors 82 on the opposite arm when both arms are in the closed configuration.

The energy director 82 may be an electrode that is designed to pass monopolar, bipolar or tripolar current into the tissue to be treated. In this configuration the electrode is adapted to pass the electrical current through the tissue in order to heat the tissue. The degree of heating of the tissue 60 is determined by the frequency and amplitude of radio frequency waves, the duration of the energy application, the clamping force of the jaw member 20, and the integrity of the electrical connection between the electrode and the tissue. Electrode design and configuration as well as the materials and controls for effective tissue coagulation and cutting are well described in the prior art and it is the intent of this invention to utilize technology that is well understood by those skilled in the art.

Figure 6A:
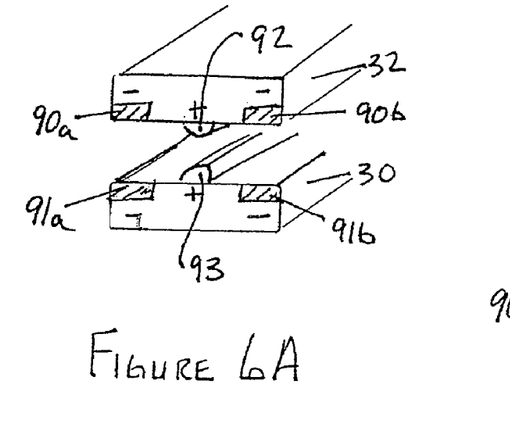
FIG. 6A is a diagrammatical end view of the pivotable and stationary arms showing one embodiment of the energy directors.

However as shown in FIGS. 6 and 7, the arrangement of the electrodes and the order in which these electrodes are activated may have some advantages over prior art electrode design and operation. Referring specifically to FIG. 6A, the arms 30 and 32 are shown in a diagrammatic drawing in what represents a generally closed configuration that would confine a portion of tissue 60 between the two arms 30 and 32. In this drawing the stationary arm 30 is shown as a separate arm. This arm 30 may be a separate arm or integrally formed as a part of the elongated body 16. Several energy directors are shown which are electrodes adapted to pass a monopolar, bipolar or tripolar energy source. Outer electrodes 90a and 90b and central electrode 92 are shown coupled to the treatment side of the pivotable arm 32. Similarly, Outer electrodes 91a and 91b and central electrode 93 are shown coupled to the treatment side of the stationary arm 30. The outer electrodes 90a-b and 91a-b are shown in a couplet arrangement, where electrodes 90a and 91a and 90b and 91b are directly opposed from each other as an electrode pair when the arms 30 and 32 are in a closed configuration. Likewise central electrodes 92 and 93 are shown in a couplet arrangement, where electrodes 92 and 93 are directly opposed from each other as an electrode pair when the arms 30 and 32 are in a closed configuration.

Figure 6B:
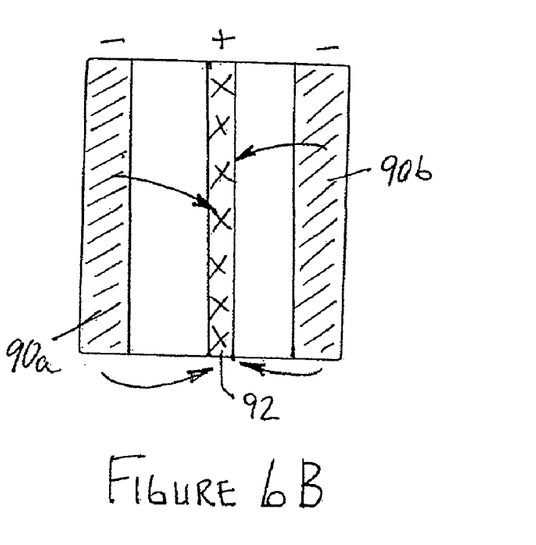
FIG. 6B is a diagrammatical underside view of the pivotable arm showing the embodiment of the energy directors shown in FIG. 6A.

The electrodes may have different polarities depending on the treatment intention for the tissue positioned between the arms. For example if the tissue is to be sealed then one electrode polarity configuration may be used and if tissue is to be dissected then another electrode polarity may be used. In addition to the polarity of the electrode, various combinations of electrodes may be turned on or off to vary the application of the energy. For example, in a bipolar energy configuration, the outer electrodes 90a-b and 91a-b may be considered negatively charged electrodes and the central electrodes 92 and 93 positively charged electrodes. FIG. 6B shows a diagrammatic view of the underside of the pivotable arm 32. When a current is introduced to these electrodes on both arms 30 and 32, current flow will be as indicated by the arrows and will generally flow from the outer electrodes to the central electrodes. This configuration of electrodes including the flow direction and the polarity may be useful for a particular tissue treatment option such as sealing or coagulation.

Figure 7A:
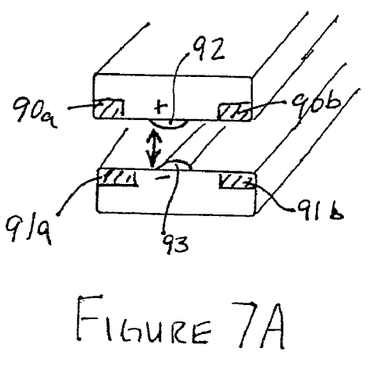
FIG. 7A is a diagrammatical end view of the pivotable and stationary arms showing another embodiment of the energy directors.
Figure 7B:
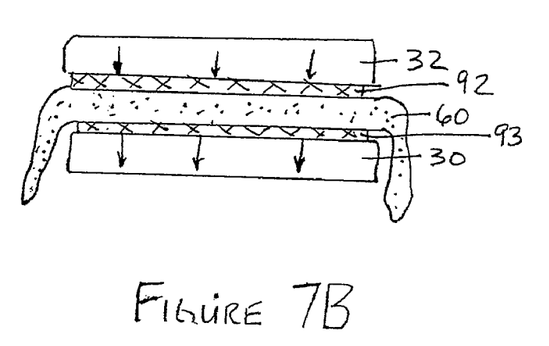
FIG. 7B is a diagrammatical side view of the pivotable and stationary arms showing the embodiment of the energy directors shown in FIG. 7A.

Referring now to FIGS. 7A and 7B, the arms 30 and 32 are shown in a generally closed configuration that confines a portion of tissue 60 between the two arms 30 and 32. The layout of the electrode couplets are the same as shown in FIGS. 6A and 6B. However in this example, different pairs of electrodes are activated to achieve a different treatment result. For example, in a bipolar energy configuration, the outer electrodes 90a-b and 91a-b are inactivated and no current or energy is applied to these electrodes. However when a current is introduced to the central electrodes 92 and 93 with one electrode having a negative charge and the other electrode having a positive charge, current flow will be as indicated by the arrows and will generally flow from central electrode 92 positioned on the pivotable arm, through the tissue 60 to central electrode 93 positioned on the stationary arm. This configuration of electrodes including the flow direction and the polarity may be useful for a particular tissue treatment option such as dissection of tissue. Of course the reverse configuration is possible with the same treatment result with one electrode 93 having a negative charge and the other electrode 92 a positive charge. In this example the electrical current will generally flow from the central electrode 93 positioned on the stationary arm, through the tissue 60 to the central electrode 92 positioned on the pivotable arm. In another embodiment of the invention the energy director 82 may be used to direct other types of energy or treatment modalities to the tissue. The energy director 82 may be used to pass high frequency ultrasound into the tissue to effectively seal or cut tissue 60. This type of energy has been shown to be effective in treating tissue. Alternatively the energy director may be a resistance dc heater. In this embodiment the director 82 receives a low voltage dc current that causes a resistance element in the energy director 82 to heat up. This heat may be controlled by the operator and may be used to seal or cut through tissue adjacent to the director 82. The effectiveness of this energy application may be dependent upon similar factors as the electrodes previously described. That is current levels of the electricity being passed, the duration of the current application, the clamping force of the jaw member 20, and the integrity of the electrical connection between the electrode and the tissue as well as other factors may affect the effectiveness of the heat application. However this invention may effectively facilitate the use of many energy application alternatives because the clamping force, which also affects the integrity of the electrical connection between the electrode and the tissue, can be precisely controlled by the capture sleeve.

In another embodiment the energy director may be a cryogenic tip that delivers low temperatures to the energy directors to seal and or cut tissue using cold temperatures. In still another embodiment the energy director may be used to deliver ablation therapy to targeted tissue positioned between the jaw member 20. In this configuration the director 82 may be used to generally ablate tissue in contact with the director. This ablation or tissue modification may be achieved using known ablation therapies such as cold, heat, chemical or electrical ablation of tissue adjacent to the arms 30 and 32.

In another embodiment the instrument may be made from materials that produce minimal amounts of glare when illuminated by the light source of an endoscope. This may be particularly important to reduce the amount of reflected glare from instruments so the visual surgical field is not impaired. Additionally, the instrument might be coated with anti-glare coating after the instrument is made. These coatings may also reduce unwanted glare from the surgical field and thereby improve the efficacy of this reverse acting sealer and cutter.

Another embodiment of the invention is a method for sealing and dissecting tissue by the use of a reverse acting surgical instrument. This surgical instrument has both sealing and dissecting capabilities and may be useful in the sealing or removal of tissue in endoscopic procedures, preferably NOTES procedures. The instrument may be introduced into the body through a natural body orifice or maybe introduced using conventional endoscopic or laparoscopic insertion techniques. The instrument maybe introduced directly into tissue using the tunneling tip to make an entrance conduit or the instrument may be introduced as a part of an introducer system. The instrument is prepared for the introduction by retracting the closure sheath and moving the jaw member 20 into a closed configuration. This configuration presents the lowest cross sectional profile for introduction into the body. The instrument 10 is advanced to the target surgical site as a stand alone device or as part of an endoscopic system. The introduction of the instrument may be facilitated by the use of articulated and steerable portions of the body. Once the instrument is positioned at the target site the closure sheath 18 is advanced in a distal direction. Once the treatment window aligns with pivotable arm 32, the arm 32 begins to open into a generally open configuration. With the jaw member 20 in an open configuration, the instrument can be manipulated so that targeted body tissue may be positioned in the jaw member 20. The tissue may be captured in the jaw member by sliding the closure sleeve 18 in a proximal direction to move the hinged jaw into a generally closed configuration. In this configuration the tissue may be confined within the hinged jaw and the tissue modification member can be activated to modify the characteristics of the tissue. The tissue may be modified as described previously using ultrasound, heat, dc current, monopolar, bipolar or tripolar energy sources, mechanical or chemical ablation, cutters or dissectors. After the tissue has been manipulated, the closure sheath is moved in a proximal direction to again place the jaw member 20 into a closed configuration suitable for removal from the body. The method of tissue manipulation may include altering the polarity and the number of energy directors that are activated so that various results are achieved. Some combination of energy director activation may result in sealing tissue while other combinations of energy director activation may result in dissecting tissue.

In one embodiment of the method the tissue activation step includes cutting tissue with a blade attached to the pivotable arm 32. In another embodiment of the method the tissue activation step includes cutting tissue with a moveable cutter. In still another embodiment of the method the tissue activation step includes energizing at least one energy director positioned on at least one of the arms so that when energy is passed through this director, body tissue located in the jaw member is sealed, dissected or sealed and then dissected.

This invention has been described and specific examples of the invention have been portrayed. The use of those specifics is not intended to limit the invention in anyway. Additionally, to the extent that there are variations of the invention, which are within the spirit of the disclosure or equivalent to the inventions found in the claims, it is our intent that this patent will cover those variations as well.

What is claimed is:

1. A device having distal and proximal end portions comprising:
   an elongated body having a longitudinal axis and an outside diameter,
   a jaw member positioned at the distal end portion, said jaw member having a stationary arm formed in the body and a pivotable arm coupled to the distal end portion of the body, a pivot point of said pivotable arm being fixed relative to the longitudinal axis, the pivotable arm including a pivot end disposed at the pivot point and a free end distanced from the pivot point, the free end being closer to the proximal portion of the device than the pivot end,
   a moveable closure sleeve disposed at least partially about the body, said closure sleeve configured to extend to the distal end of the elongated body and also configured such that coaxial movement of the sleeve along the longitudinal axis causes the jaw member to open or close, the closure sleeve terminating at a distal part of the closure sleeve in a closure ring which completely circumscribes the elongated body, the closure ring being urged against a distal part of the pivotal arm to move the pivotal arm toward the stationary arm when the closure sleeve is moved proximally relative to the elongated body;
   further comprising a spring, said spring biasing the pivotable arm in an open configuration; and
   wherein the jaw member is positioned in a cavity in the elongated body, said cavity defining an area having a reduced cross sectional area compared to the more proximal portions of the elongated body, wherein the jaw member has a diameter substantially equivalent to the outside diameter of the elongated body when in a closed position.

2. The device of claim 1 configured such that the jaw opening generally opens toward the proximal end portion of the elongated body.

3. The device of claim 2 adapted so that movement of the closure sleeve causes the pivotable arm to open or close.

4. The device of claim 3, wherein the closure ring defines the distal edge of a treatment window positioned at the distal end portion of the elongated body, said treatment window defining an opening in the closure sleeve and adapted to have a similar profile as the cavity, said treatment window aligned with the cavity when the jaw member is in an open position.

5. The device of claim 1 wherein the elongated body is adapted to transmit a torque such that the jaw member can be rotated by applying a torque to the proximal end portion and wherein the jaw member is adapted to articulate and rotate to facilitate capturing body tissue in the jaw member.

6. The device of claim 1 having a tunneling tip positioned at the distal end portion and adapted to facilitate placement of the instrument through body tissue.

7. The device of claim 1 further comprising at least one tissue modification member on the stationary arm, the pivotable arm, the elongate body or a combination thereof, said modification member capable of sealing, dissecting or a combination of sealing and dissecting body tissue positioned between the stationary arm and the pivotable arm.

8. The device of claim 7 wherein the modification member is a stationary dissecting blade attached to the pivotable arm, said blade configured to dissect tissue positioned between the pivotable arm and the stationary arm.

9. The device of claim 7 wherein the modification member is a moveable dissecting blade positioned inside the distal end portion of the elongate body, said blade adapted to slide along the longitudinally axis of the elongate body to dissect body tissue confined between the arms of the jaw member.

10. The device of claim 7, the modification member further comprising at least one energy director, the energy director adapted so that when energy from an energy source is passed through the energy director, body tissue confined between the two arms is sealed, dissected, or a combination of sealed and dissected.

11. The device of claim 10 comprising an ultrasonic source, a monopolar, bipolar or tripolar source or a dc current source.

12. The device of claim 11 further comprising a controller such that the order of sealing and dissecting can be controlled by an operator.

13. The device of claim 11, further comprising at least a first and a second energy director attached to each of the pivotable arm and the stationary arm, the energy directors aligned so that when the jaw member closes the first energy director opposes the second energy director.

14. The device of claim 13 wherein when energy from the energy source is passed between the opposing pairs, body tissue located in between the two arms is sealed, dissected or a combination of sealed and dissected.

15. The device of claim 13 wherein when energy from the energy source is passed between the first energy director attached to the pivotable arm and the second energy director attached to a stationary arm, body tissue located in between the two arms is sealed, dissected or a combination of sealed and dissected.

16. The device of claim 1 further comprising an anti-glare coating applied to the distal end portion of the elongated body.

17. A surgical instrument for sealing or dissecting body tissue having distal and proximal end portions comprising:

an elongated body having a reverse acting jaw member coupled at the distal end portion with the jaw member biased in an open position, the jaw member formed by at least one stationary arm which is a part of the elongated body and at least one second arm that is pivotably connected at the distal end portion and generally oriented toward the proximal end portion, said second arm having a free end and a pivot point distal to the free end and that is fixed on the longitudinal axis of the elongated body, the jaw member configured to be activated by a closure sleeve, said closure sleeve configured to extend to the distal end of the elongated body and be coaxially disposed about the elongated body such that the jaw is opened and closed by movement of the sleeve along a longitudinal axis of the elongated body, the closure sleeve distally terminating in a hollow closure ring surrounding the elongated body, the closure ring being in a first position that is distal to the pivot point when the jaw member is in the open position, the closure ring riding against the second arm to urge it to pivot toward the stationary arm when the closure sleeve is moved proximally relative to the elongated body from the first position toward a second position that is proximal to the first position;

further comprising a spring, said spring biasing said second arm in an open configuration; and wherein the reverse acting jaw member is positioned in a cavity in the elongated body, said cavity defining an area having a reduced cross sectional area compared to the more proximal portions of the elongated body, wherein the reverse acting jaw member has a diameter substantially equivalent to an outside diameter of the elongated body when in a closed position.

18. The instrument of claim 17 wherein the sleeve is a tube that surrounds the elongate body, the sleeve having a treatment window defined by an opening in the sleeve sized and adapted so that when the treatment window is aligned along the longitudinal axis with the jaw member, the jaw member is in an open configuration and when the sleeve is moved toward the proximal end portion, the jaw member is moved toward a closed configuration.

19. The instrument of claim 17 wherein the elongated body is adapted to transmit a torque such that the jaw member can be rotated by applying a torque to the proximal end portion and wherein the jaw member is adapted to articulate and rotate to facilitate capturing body tissue in the jaw member.

20. The instrument of claim 19 having a tunneling tip positioned at the distal end portion and adapted to facilitate placement of the instrument through body tissue.

21. The instrument of claim 19 further comprising at least one tissue modification member on the stationary arm, the second pivotable arm, the elongate body or a combination thereof, said modification member capable of sealing, dissecting or a combination of sealing and dissecting body tissue positioned between the stationary arm and the second pivotable arm.

22. The instrument of claim 21 wherein the tissue modification member is a stationary cutting blade attached to the pivotable arm, said blade configured to dissect tissue positioned between the pivotable arm and the stationary arm.

23. The instrument of claim 21 wherein the tissue modification member is a moveable dissecting blade positioned inside the distal end portion of the elongate body, said blade adapted to slide along a longitudinally axis of the elongate body to dissect body tissue confined between the arms of the jaw member.

24. The instrument of claim 21, the tissue modification member further comprising at least one energy director, the energy director adapted so that when energy from an energy source is passed through the energy director, body tissue located in between the two arms is sealed, dissected, or a combination of sealed and dissected.

25. The instrument of claim 24 comprising an ultrasonic source, a monopolar, bipolar or tripolar source or a dc current source.

26. The instrument of claim 25 further comprising a controller such that the order of sealing and dissecting can be controlled by an operator.

27. The instrument of claim 25 further comprising at least a first and a second energy director attached to each of the pivotable arm and the stationary arm, the energy directors aligned so that when the jaw member closes the at least first energy directors opposes the at least second energy director.

28. The instrument of claim 27 wherein when energy from the energy source is passed between the opposing pairs, body tissue located in between the two arms is sealed, dissected or a combination of sealed and dissected.

29. The instrument of claim 27 wherein when energy from the energy source is passed between the first energy director attached to the pivotable arm and the second energy director attached to a stationary arm, body tissue located in between the two arms is sealed, dissected or a combination of sealed and dissected.

* * * * *